United States Patent
Spence et al.

(10) Patent No.: US 10,653,519 B2
(45) Date of Patent: May 19, 2020

(54) MITRAL REPAIR AND REPLACEMENT DEVICES AND METHODS

(71) Applicant: Mitral Valve Technologies Sarl, Nyon (CH)

(72) Inventors: Paul A. Spence, Louisville, KY (US); Landon H. Tompkins, La Grange, KY (US)

(73) Assignee: Mitral Valve Technologies Sarl, Nyon (CH)

( * ) Notice: Subject to any disclaimer, the term of this patent is extended or adjusted under 35 U.S.C. 154(b) by 157 days.

(21) Appl. No.: 16/029,355

(22) Filed: Jul. 6, 2018

(65) Prior Publication Data

US 2018/0311038 A1   Nov. 1, 2018

Related U.S. Application Data

(62) Division of application No. 14/850,822, filed on Sep. 10, 2015, now Pat. No. 10,016,272.

(Continued)

(51) Int. Cl.
*A61F 2/24* (2006.01)

(52) U.S. Cl.
CPC .......... *A61F 2/2409* (2013.01); *A61F 2/2418* (2013.01); *A61F 2/2442* (2013.01);
(Continued)

(58) Field of Classification Search
CPC .... A61F 2/2409; A61F 2/2418; A61F 2/2427; A61F 2/2442; A61F 2/2445; A61F 2/2469; A61F 2230/0091
See application file for complete search history.

(56) References Cited

U.S. PATENT DOCUMENTS

| | | |
|---|---|---|
| 3,564,617 A | 2/1971 | Sauvage et al. |
| 4,035,849 A | 7/1977 | Angell et al. |

(Continued)

FOREIGN PATENT DOCUMENTS

| | | |
|---|---|---|
| CN | 1684644 A | 10/2005 |
| CN | 1714766 A | 1/2006 |

(Continued)

OTHER PUBLICATIONS

Kempfert et al., "Minimally invasive off-pump valve-in-a-ring implantation: the atrial transcatheter approach for re-operative mitral valve replacement after failed repair," European Journal of Cardiothoracic Surgery, 2009, 35:965-969.

(Continued)

*Primary Examiner* — Dinah Baria
(74) *Attorney, Agent, or Firm* — Calfee, Halter & Griswold LLP; Hans P. Smith

(57) ABSTRACT

An implant and method for repairing and/or replacing functionality of a native mitral valve are in various embodiments configured to reduce or eliminate mitral regurgitation and residual mitral valve leakage. A coiled anchor with a central turn that reduces in size upon implantation is used to approximate the amount of reduction in the size and the reshaping of the native mitral annulus to reduce valve leakage. A clip can be further applied to the native valve leaflets to reduce the size of the native mitral annulus and leakage therethrough. A prosthetic heart valve can be implanted in the coiled anchor to replace and further improve functionality of the valve. In some cases, the prosthetic valve can be implanted in a clipped valve, where the clip is detached from one of the native valve leaflets to provide space for the prosthetic valve to expand.

14 Claims, 8 Drawing Sheets

Related U.S. Application Data

(60) Provisional application No. 62/073,088, filed on Oct. 31, 2014, provisional application No. 62/049,432, filed on Sep. 12, 2014.

(52) U.S. Cl.
CPC .... *A61F 2/2463* (2013.01); *A61F 2210/0014* (2013.01); *A61F 2220/0025* (2013.01); *A61F 2230/0091* (2013.01); *A61F 2250/006* (2013.01); *A61F 2250/0039* (2013.01)

(56) References Cited

U.S. PATENT DOCUMENTS

| | | |
|---|---|---|
| 4,490,859 A | 1/1985 | Black et al. |
| 4,512,338 A | 4/1985 | Balko et al. |
| 5,059,177 A | 10/1991 | Towne et al. |
| 5,403,305 A | 4/1995 | Sauter et al. |
| 5,411,552 A | 5/1995 | Andersen et al. |
| 5,443,500 A | 8/1995 | Sigwart |
| 5,554,185 A | 9/1996 | Block et al. |
| 5,840,081 A | 11/1998 | Andersen et al. |
| 5,957,949 A | 9/1999 | Leonhardt et al. |
| 6,120,534 A | 9/2000 | Ruiz |
| 6,168,614 B1 | 1/2001 | Andersen et al. |
| 6,235,042 B1 | 5/2001 | Katzman |
| 6,306,141 B1 | 10/2001 | Jervis |
| 6,406,492 B1 | 6/2002 | Lytle |
| 6,409,758 B2 | 6/2002 | Stobie et al. |
| 6,419,696 B1 | 7/2002 | Ortiz et al. |
| 6,432,134 B1 | 8/2002 | Anson et al. |
| 6,458,153 B1 | 10/2002 | Bailey et al. |
| 6,527,979 B2 | 3/2003 | Constantz |
| 6,582,462 B1 | 6/2003 | Andersen et al. |
| 6,625,578 B2 | 9/2003 | Spaur et al. |
| 6,652,578 B2 | 11/2003 | Bailey et al. |
| 6,676,698 B2 | 1/2004 | McGuckin, Jr. et al. |
| 6,730,121 B2 | 5/2004 | Ortiz et al. |
| 6,797,002 B2 | 9/2004 | Spence et al. |
| 6,908,481 B2 | 6/2005 | Cribier |
| 6,971,998 B2 | 12/2005 | Rosenman et al. |
| 7,018,408 B2 | 3/2006 | Bailey et al. |
| 7,037,334 B1 | 5/2006 | Hlavka et al. |
| 7,077,861 B2 | 7/2006 | Spence |
| 7,101,395 B2 | 9/2006 | Tremulis et al. |
| 7,125,421 B2 | 10/2006 | Tremulis et al. |
| 7,166,126 B2 | 1/2007 | Spence et al. |
| 7,166,127 B2 | 1/2007 | Spence et al. |
| 7,404,824 B1 | 7/2008 | Webler et al. |
| 7,431,726 B2 | 10/2008 | Spence et al. |
| 7,445,632 B2 | 11/2008 | McGuckin, Jr. et al. |
| 7,527,646 B2 | 5/2009 | Rahdert et al. |
| 7,585,321 B2 | 9/2009 | Cribier |
| 7,618,446 B2 | 11/2009 | Andersen et al. |
| 7,618,449 B2 | 11/2009 | Tremulis et al. |
| 7,737,060 B2 | 6/2010 | Strickler et al. |
| 7,758,639 B2 | 7/2010 | Mathis |
| 7,780,726 B2 | 8/2010 | Seguin |
| 7,785,366 B2 | 8/2010 | Maurer et al. |
| 7,942,927 B2 | 5/2011 | Kaye et al. |
| 7,951,195 B2 | 5/2011 | Antonsson et al. |
| 7,955,385 B2 | 6/2011 | Crittenden |
| 8,016,882 B2 | 9/2011 | Macoviak et al. |
| 8,052,750 B2 | 11/2011 | Tuval et al. |
| 8,092,520 B2 | 1/2012 | Quadri |
| 8,128,691 B2 | 3/2012 | Keranen |
| 8,236,049 B2 | 8/2012 | Rowe et al. |
| 8,323,335 B2 | 12/2012 | Rowe et al. |
| 8,377,115 B2 | 2/2013 | Thompson |
| 8,398,708 B2 | 3/2013 | Meiri et al. |
| 8,449,605 B2 | 5/2013 | Lichtenstein et al. |
| 8,449,606 B2 | 5/2013 | Eliasen et al. |
| 8,657,872 B2 | 2/2014 | Seguin |
| 8,663,322 B2 | 3/2014 | Keranen |
| 8,672,998 B2 | 3/2014 | Lichtenstein et al. |
| 8,734,507 B2 | 5/2014 | Keranen |
| 8,795,352 B2 | 8/2014 | O'Beirne et al. |
| 8,986,373 B2 | 3/2015 | Chau et al. |
| 9,078,747 B2 | 7/2015 | Conklin |
| 9,095,434 B2 | 8/2015 | Rowe |
| 9,119,718 B2 | 9/2015 | Keranen |
| 9,237,886 B2 | 1/2016 | Seguin et al. |
| 9,364,326 B2 | 6/2016 | Yaron |
| 9,463,268 B2 | 10/2016 | Spence |
| 9,474,599 B2 | 10/2016 | Keranen |
| 9,622,863 B2 | 4/2017 | Karapetian et al. |
| 10,016,272 B2 | 7/2018 | Spence et al. |
| 2002/0045936 A1 | 4/2002 | Moe |
| 2002/0173841 A1 | 11/2002 | Ortiz et al. |
| 2003/0167089 A1 | 9/2003 | Lane |
| 2003/0225420 A1 | 12/2003 | Wardle |
| 2004/0167620 A1 | 8/2004 | Ortiz et al. |
| 2004/0260389 A1 | 12/2004 | Case et al. |
| 2005/0096736 A1 | 5/2005 | Osse et al. |
| 2005/0119735 A1 | 6/2005 | Spence et al. |
| 2005/0137691 A1 | 6/2005 | Salahieh et al. |
| 2005/0203614 A1 | 9/2005 | Forster et al. |
| 2005/0203617 A1 | 9/2005 | Forster et al. |
| 2006/0025857 A1 | 2/2006 | Bergheim et al. |
| 2006/0265056 A1 | 11/2006 | Nguyen et al. |
| 2007/0185572 A1 | 8/2007 | Solem et al. |
| 2007/0203575 A1 | 8/2007 | Forster et al. |
| 2007/0213813 A1 | 9/2007 | Von Segesser et al. |
| 2007/0232898 A1 | 10/2007 | Huynh et al. |
| 2007/0244553 A1 | 10/2007 | Rafiee et al. |
| 2007/0265700 A1 | 11/2007 | Eliasen et al. |
| 2008/0004697 A1 | 1/2008 | Lichtenstein et al. |
| 2008/0033542 A1 | 2/2008 | Antonsson et al. |
| 2008/0125853 A1 | 5/2008 | Bailey et al. |
| 2008/0208330 A1 | 8/2008 | Keranen |
| 2008/0228265 A1 | 9/2008 | Spence et al. |
| 2008/0243245 A1 | 10/2008 | Thambar et al. |
| 2008/0275503 A1 | 11/2008 | Spence et al. |
| 2009/0177278 A1 | 7/2009 | Spence |
| 2009/0234318 A1 | 9/2009 | Loulmet et al. |
| 2009/0259307 A1 | 10/2009 | Gross et al. |
| 2009/0276038 A1 | 11/2009 | Tremulis et al. |
| 2009/0276040 A1 | 11/2009 | Rowe et al. |
| 2009/0299471 A1 | 12/2009 | Keranen |
| 2009/0319037 A1 | 12/2009 | Rowe et al. |
| 2010/0076549 A1 | 3/2010 | Keidar et al. |
| 2010/0145440 A1 | 6/2010 | Keranen |
| 2010/0152839 A1 | 6/2010 | Shandas et al. |
| 2010/0161047 A1 | 6/2010 | Cabiri |
| 2010/0217382 A1 | 8/2010 | Chau et al. |
| 2010/0312333 A1 | 12/2010 | Navia et al. |
| 2010/0318183 A1 | 12/2010 | Keranen |
| 2010/0318184 A1 | 12/2010 | Spence |
| 2010/0331971 A1 | 12/2010 | Keranen et al. |
| 2010/0331973 A1 | 12/2010 | Keranen |
| 2011/0098802 A1 | 4/2011 | Braido et al. |
| 2011/0106247 A1 | 5/2011 | Miller et al. |
| 2011/0137397 A1 | 6/2011 | Chau et al. |
| 2011/0178597 A9 | 7/2011 | Navia et al. |
| 2011/0208298 A1 | 8/2011 | Tuval et al. |
| 2011/0218621 A1 | 9/2011 | Antonsson et al. |
| 2011/0224785 A1 | 9/2011 | Hacohen |
| 2011/0245911 A1 | 10/2011 | Quill et al. |
| 2011/0288634 A1 | 11/2011 | Tuval et al. |
| 2011/0295361 A1 | 12/2011 | Claiborne, III et al. |
| 2011/0319989 A1 | 12/2011 | Lane et al. |
| 2011/0319990 A1 | 12/2011 | Macoviak et al. |
| 2012/0016464 A1 | 1/2012 | Seguin |
| 2012/0053680 A1 | 3/2012 | Bolling et al. |
| 2012/0059458 A1 | 3/2012 | Buchbinder et al. |
| 2012/0150287 A1 | 6/2012 | Forster et al. |
| 2012/0310328 A1 | 12/2012 | Olson et al. |
| 2012/0316643 A1 | 12/2012 | Keranen |
| 2013/0006352 A1 | 1/2013 | Yaron |
| 2013/0310917 A1 | 11/2013 | Richter et al. |
| 2013/0310928 A1 | 11/2013 | Morriss et al. |
| 2014/0074229 A1 | 3/2014 | Figulla et al. |
| 2014/0172070 A1 | 6/2014 | Seguin |
| 2014/0236287 A1 | 8/2014 | Clague et al. |

(56) References Cited

U.S. PATENT DOCUMENTS

| | | | |
|---|---|---|---|
| 2014/0257466 | A1 | 9/2014 | Board et al. |
| 2014/0379074 | A1 | 12/2014 | Spence et al. |
| 2015/0230921 | A1 | 8/2015 | Chau et al. |
| 2015/0282931 | A1 | 10/2015 | Brunnett et al. |
| 2015/0335428 | A1 | 11/2015 | Keranen |
| 2015/0374493 | A1 | 12/2015 | Yaron et al. |
| 2016/0074165 | A1 | 3/2016 | Spence et al. |
| 2016/0095705 | A1 | 4/2016 | Keranen et al. |
| 2016/0184095 | A1 | 6/2016 | Spence et al. |
| 2016/0199177 | A1 | 7/2016 | Spence et al. |
| 2016/0256276 | A1 | 9/2016 | Yaron |
| 2017/0007399 | A1 | 1/2017 | Keranen |
| 2017/0007402 | A1 | 1/2017 | Zerkowski et al. |

FOREIGN PATENT DOCUMENTS

| | | |
|---|---|---|
| CN | 101588771 A | 11/2009 |
| DE | 19532846 A1 | 3/1997 |
| DE | 19907646 A1 | 8/2000 |
| EP | 0592410 A1 | 4/1994 |
| EP | 0850607 A1 | 7/1998 |
| EP | 1827314 A1 | 9/2007 |
| EP | 2072027 A1 | 6/2009 |
| WO | 9117720 A1 | 11/1991 |
| WO | 2005084595 A1 | 9/2005 |
| WO | 2005102015 A2 | 11/2005 |
| WO | 2007067942 A1 | 6/2007 |
| WO | 2009134701 A2 | 11/2009 |
| WO | 2010057262 A1 | 5/2010 |
| WO | 2010121076 A2 | 10/2010 |
| WO | 2013110722 A2 | 8/2013 |
| WO | 2013114214 A2 | 8/2013 |

OTHER PUBLICATIONS

Webb et al., "Transcatheter Valve-in-Valve Implantation for Failed Bioprosthetic Heart Valves," Journal of the American Heart Association, 11, Apr. 27, 2010.

Webb et al., "Mitral Valve in Valve," TCT Sep. 2009, Live Case: 30 Minutes, St. Paul's Hospital/University of British Columbia.

Wenaweser et al., "Percutaneous Aortic Valve Replacement for Severe Aortic Regurgitation in Degenerated Bioprosthesis: The First Valve Procedure Using Corevalve Revalving System," Catheterization and Cardiovascular Interventions, 70:760-764, 2007.

Cheung et al,"Transapical Transcatheter Mitral Valve-in-Valve Implantation in a Human," The Society of Thoracic Surgeons, 2009.

Cheung et al, Live Case Transmissions, NYHA III CHF, Case Summary, Sep. 23, 2010, St. Paul's Hospital/University of British Columbia.

Shuto et al., "Percutaneous Transvenous Melody Valve-in-Ring Procedure for Mitral Valve Replacement," J AM Coll Cardiol, 58(24): 2475-2480, 2011.

Descoutures et al., "Transcatheter Valve-in-Ring Implantation After Failure of Surgical Mitral Repair," European Journal of Cardio-Thoracic Surgery 44, e8-e15, 2013.

Weger et al., "First-in-Man Implantation of a Trans-Catheter Aortic Valve in a Mitral Annuloplasty Ring: Novel Treatment Modality for Failed Mitral Valve Repair," European Journal of Cardio-Thoracic Surgery 39, 1054-1056, 2011.

Walther et al., "Human Minimally Invasive Off-Pump Valve-in-a-Valve Implantation," Case Reports, The Society of Thoracic Surgeons, 2008.

Walther et al., "Valve-in-a-Valve Concept for Transcatheter Minimally Invasive Repeat Xenograph Implantation," Preclinical Studies, Journal of the American College of Cardiology, 2007.

Himbert et al., "Transseptal Implantation of a Transcatheter Heart Valve in a Mitral Annuloplasty Ring to Treat Mitral Repair Failure," Circulation Cardiovascular Interventions, American Heart Association, 2011.

Himbert, Dominique, "Transvenous Mitral Valve Repair Replacement After Failure of Surgical Ring Annuloplasty," Research Correspondence, Journal of the American College of Cardiology, 2012.

Casselman et al., "Reducing Operative Morality in Valvular Reoperations: The "valve in ring" Procedure," Brief Technique Reports, The Journal of Thoracic and Cardiovascular Surgery, vol. 141, No. 5. May 2011.

Ma et al., "Double-Crowned Valved Stents for Off-Pump Mitral Valve Replacement," European Journal of Cardio-Thoracic Surgery, 28, 194-199, 2005.

Bonhoeffer et at., "Percutaneous Replacement of Pulmonary valve in a Right-Ventricle to Pulmonary-Artery Prosthetic Conduit with Valve Dysfunction," Early Report, The Lancet, vol. 356, Oct. 21, 2000.

International Search Report from corresponding PCT case No. PCT/IB2015/000901 dated Feb. 15, 2015.

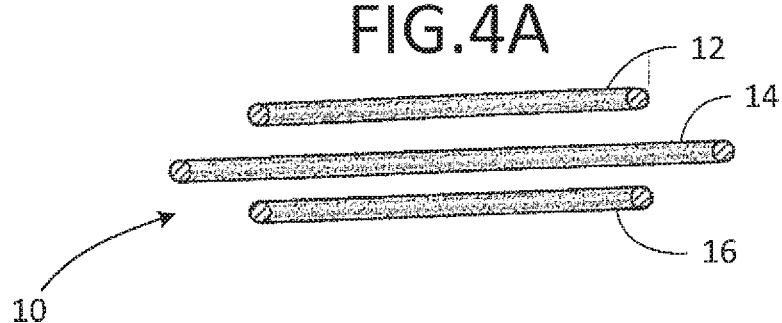
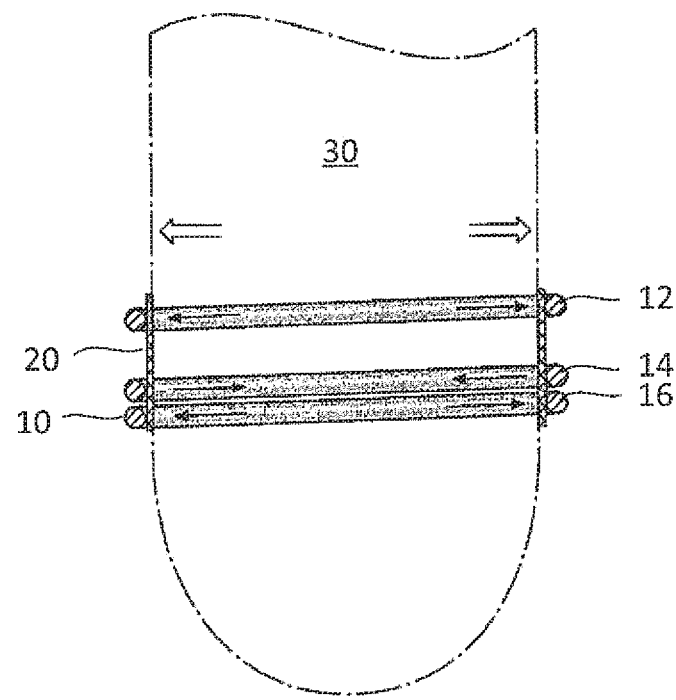
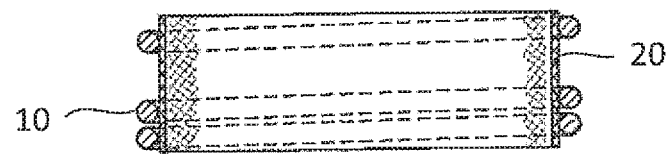

MITRAL REPAIR AND REPLACEMENT DEVICES AND METHODS

This application is a divisional application of U.S. patent application Ser. No. 14/850,822, filed Sep. 10, 2015 and assigned U.S. patent Ser. No. 10/016,272, which claims priority to and the benefit of U.S. Provisional Patent Application Ser. No. 62/049,432, filed Sep. 12, 2014, the contents of which are hereby incorporated by reference in their entirety, and also claims priority to and the benefit of U.S. Provisional Patent Application Ser. No. 62/073,088, filed Oct. 31, 2014. All of the foregoing are incorporated by reference herein in their entirety.

BACKGROUND

Field

The invention generally relates to medical devices and procedures pertaining to heart valve repair and prosthetic heart valves. More specifically, the invention relates to repair and/or replacement of heart valves that have malformations or dysfunctions. Embodiments of the invention relate to devices and methods for reshaping or resizing the native mitral valve, further treatments for reducing residual leakage at the mitral valve annulus, and replacement of the functionality of the mitral valve with a prosthetic heart valve, for example, when leakage persists.

Description of Related Art

Referring first generally to FIGS. 1 and 2, the mitral valve controls the flow of blood between the left atrium and the left ventricle of the human heart. After the left atrium receives oxygenated blood from the lungs via the pulmonary veins, the mitral valve permits the flow of the oxygenated blood from the left atrium into the left ventricle. When the left ventricle contracts, the oxygenated blood held in the left ventricle is delivered through the aortic valve and the aorta to the rest of the body. Meanwhile, the mitral valve closes during ventricular contraction, to prevent the flow of blood back into the left atrium.

The mitral valve includes an anterior leaflet and a posterior leaflet. When the left ventricle contracts, the anterior and posterior leaflets come together and the blood pressure in the left ventricle increases substantially to urge the mitral valve closed. Due to the large pressure differential between the left ventricle and the left atrium during ventricular contraction, a possibility of prolapse, or eversion of the leaflets of the mitral valve back into the atrium, arises. To prevent this, a series of chordae tendineae connect the mitral valve to the papillary muscles along opposing walls of the left ventricle. The chordae tendineae are schematically illustrated in both the heart cross-section of FIG. 1 and the top view of the mitral valve in FIG. 2. Just before and during ventricular contraction, the papillary muscles also contract and maintain tension in the chordae tendineae, to hold the leaflets of the mitral valve in the closed position and preventing them from turning inside-out and back into the atrium, thereby also preventing backflow of the oxygenated blood into the atrium.

A general shape of the mitral valve and its leaflets as seen from the left atrium is illustrated in FIG. 2. Complications of the mitral valve can potentially cause fatal heart failure. One form of valvular heart disease is mitral valve leak, also known as mitral regurgitation, characterized by the abnormal leaking of blood from the left ventricle back into the left atrium through the mitral valve.

Mitral regurgitation is a common problem, and various options to reduce or prevent mitral regurgitation that can be more easily tolerated or handled by a body of a patient have been researched.

One repair solution for a patient exhibiting mitral regurgitation or other mitral valve leakage employs a catheter procedure, where a free edge of the anterior leaflet is attached to a free edge of the posterior leaflet. The idea for this procedure was promoted by Dr. Ottavio Alfieri, who described seeing a patient who had a congenital anomaly where the anterior leaflet edge was fused to the posterior leaflet edge, and surmised that that could potentially provide a good solution to mitral regurgitation. Dr. Alfieri performed many procedures where the mitral annulus was repaired by reduction using an annuloplasty ring to reshape the native mitral valve annulus to be smaller and/or more circular or otherwise consistent, and then controlling residual leakage by an approximation and attachment of the anterior leaflet edge to the posterior leaflet edge at a desired arrangement. Performance of many leaky mitral valves can be repaired and improved by what has become known as the Alfieri procedure, utilizing a combination of annuloplasty to reduce the diameter of the mitral annulus and leaflet edge approximation.

The Alfieri procedure has led to other variations of catheter-based procedures to attach the edges of the anterior and posterior leaflets to control mitral regurgitation. In one procedure, under echocardiographic and fluoroscopic guidance, catheters are used to introduce a clip at the mitral annulus that fastens the free edge of the anterior leaflet to the free edge of the posterior leaflet. The clip and a delivery system are typically introduced in the patient's femoral vein and passed into the right side of the heart. A transseptal puncture is then carried out in the patient's heart, and the clip is advanced into the left atrium and then the left ventricle. The edges of the leaflets are then fastened together with the clip, and the delivery system is withdrawn. In other variations of the procedure, the clip and delivery system can instead be introduced into the patient's heart from one of various other access points or positions on the patient's body.

Most patients have one clip applied during such a procedure, but if the leak is severe and/or the leaflets are highly distracted, additional clips can also be applied. The clinical results have been gratifying. Many patients have exhibited a major reduction in leakage and are symptomatically much improved when compared to before undergoing the procedure.

Another option to further reduce the mitral leakage would be to combine or to supplement one of the above annuloplasty procedures with an edge to edge leaflet plication procedure to further strengthen the bond or attachment between the native mitral leaflets.

SUMMARY

However, even after undergoing one or more of the above procedures, some patients are still left with significant mitral valve leakage. This puts an increased load on the heart, and the heart can be damaged by the long-term effects of such residual valve regurgitation.

According to embodiments of the invention, a helical or coiled anchor having turns with different radii of curvature is provided to more effectively reduce and/or reshape the native mitral valve annulus, to reduce leakage at the mitral valve. After reshaping and/or resizing the native mitral annulus, if leakage is still observed, additional measures, such as edge to edge repair or other repair procedures, can be more easily or effectively applied to the restructured mitral annulus.

In another alternative to remedy continual leakage after employing one of the above annuloplasty procedures or other similar annular reduction procedure, a prosthetic mitral valve can further be implanted into the mitral valve annulus, since an annuloplasty procedure using a coiled anchor according to embodiments of the invention will result in the formation of a stable anchor or base into or against which the prosthetic mitral valve can be docked.

According to an embodiment of the invention, an implant for reshaping a native mitral valve of a heart includes a coiled anchor having a first end, a second end, and a central axis extending between the first and second ends. The coiled anchor defines an inner space coaxial with the central axis and includes a first turn defining a central portion of the inner space having a first width, a second turn connected to the central turn at the first end of the coiled anchor, the second turn defining a portion of the inner space having a width that is smaller than the first width, and a third turn connected to the central turn at the second end of the coiled anchor, the third turn defining another portion of the inner space having a width that is smaller than the first width. The coiled anchor is implantable at the native mitral valve with at least a portion of the first turn of the coiled anchor positioned in a left ventricle of the heart and around valve leaflets of the native mitral valve.

According to another embodiment of the invention, a method for delivering an implant according to the above embodiment includes positioning the coiled anchor at a native mitral valve of a heart of a patient, such that at least a portion of the first turn of the coiled anchor is positioned in a left ventricle of the heart and around valve leaflets of the native mitral valve, positioning an expandable stent at the native mitral valve through the inner space of the coiled anchor when the stent is in a collapsed state, and expanding the stent. The stent is expandable to a width that is greater than the width of the inner space defined by at least one of the second turn or the third turn when the coiled anchor is unbiased, such that a radially outward pressure is applied by the stent on the at least one of the second turn or the third turn to increase the width of the portion of the inner space defined by the at least one of the second turn or the third turn, while the width of the portion of the inner space defined by the first turn is decreased to a width that is smaller than the first width.

According to embodiments of the invention, repair and/or replacement of a diseased mitral valve can be more effectively realized by first reshaping, resizing, and/or otherwise restructuring the native mitral annulus using a helical or coiled anchor, such that additional devices and methods can be more easily or effectively applied at the reinforced mitral position.

BRIEF DESCRIPTION OF THE DRAWINGS

Further features and advantages of the invention will become apparent from the description of embodiments using the accompanying drawings. In the drawings:

FIGS. 4A-4C schematically show steps of expanding a balloon expandable stent in the coil anchor of FIGS. 3A-3B according to an embodiment of the invention;

DETAILED DESCRIPTION

Disclosed herein are various implants and other devices for repairing and/or replacing the functionality of a native mitral valve, and methods of implanting such devices. By providing such devices and methods of implanting the devices, mitral valve leakage and leakage caused by similar types of valvular heart disease can be reduced, and performance of the mitral valve can be improved.

In some embodiments, a helical or coiled anchor can be used to reduce and/or reshape the annular size of a native mitral valve, in preparation for a valve repair or a further annuloplasty procedure. In other embodiments, the helical anchor can be utilized to downsize a patient's native mitral valve annulus and to make the shape of the annulus more suitable to anchor or dock a prosthetic heart valve when valve replacement is planned. In these embodiments, one of various prosthetic valves that are capable of being mounted in stents can be used in conjunction with a helical anchor that narrows and/or reshapes the native mitral valve annulus.

Figure 1:
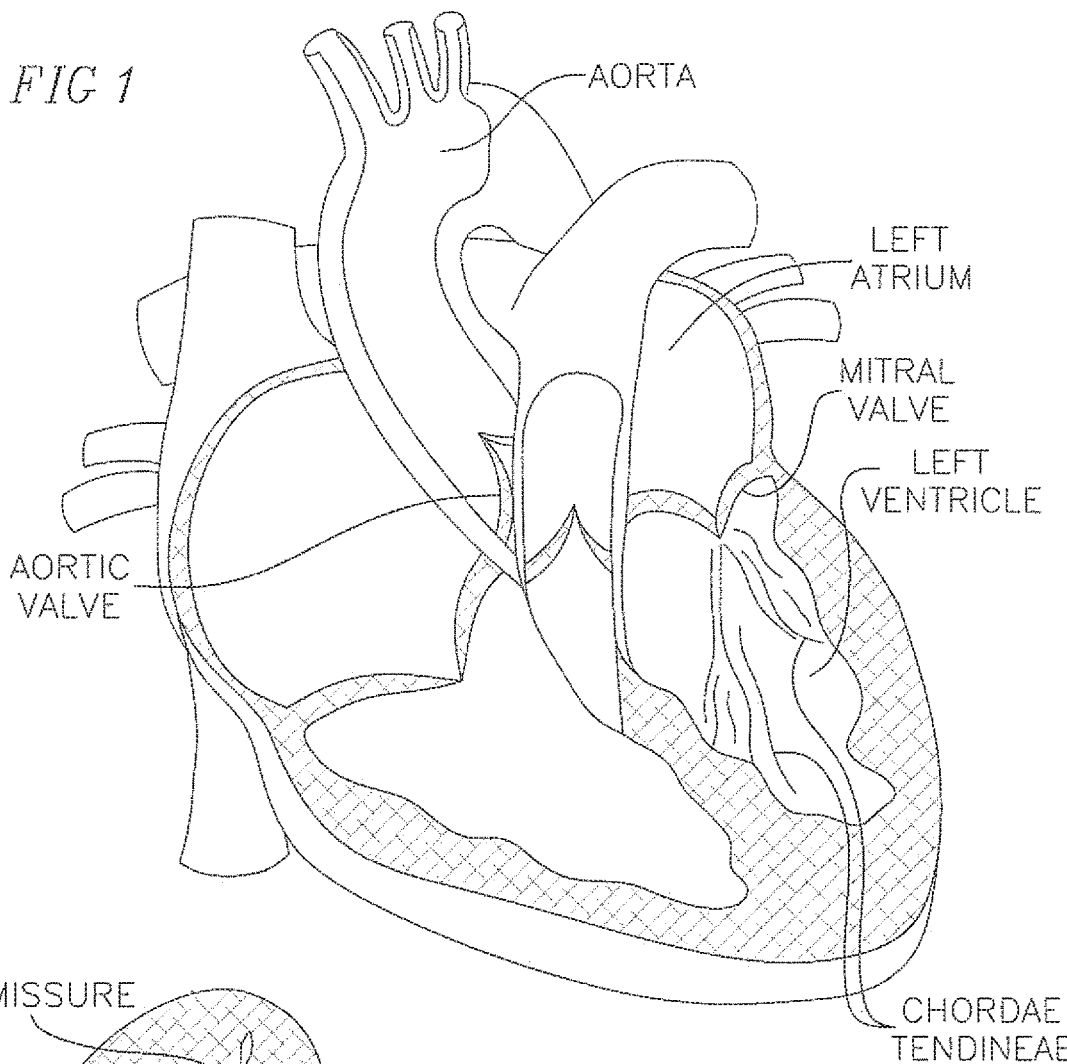
FIG. 1 shows a schematic cross-sectional view of a human heart.
Figure 2:
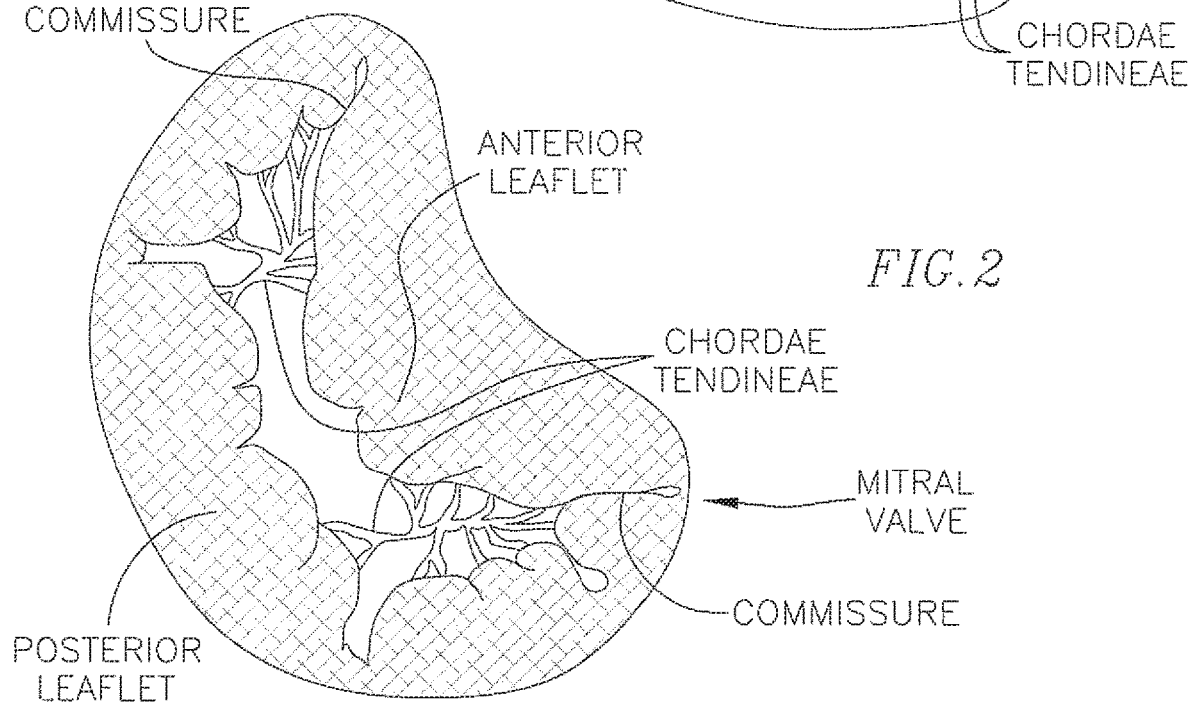
FIG. 2 shows a schematic top view of the mitral valve annulus of a heart.
Figure 3A:
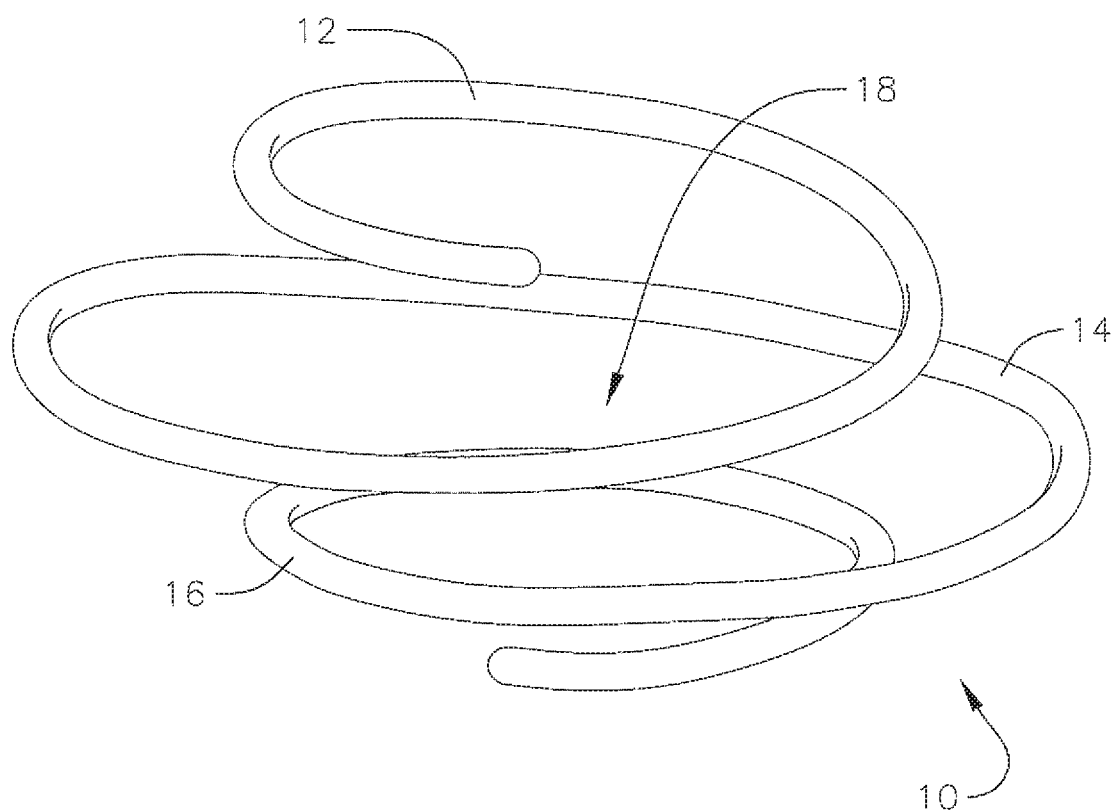
FIGS. 3A and 3B respectively show perspective and side views of a coil anchor for resizing or reshaping a native mitral valve annulus according to an embodiment of the invention.
Figure 3B:
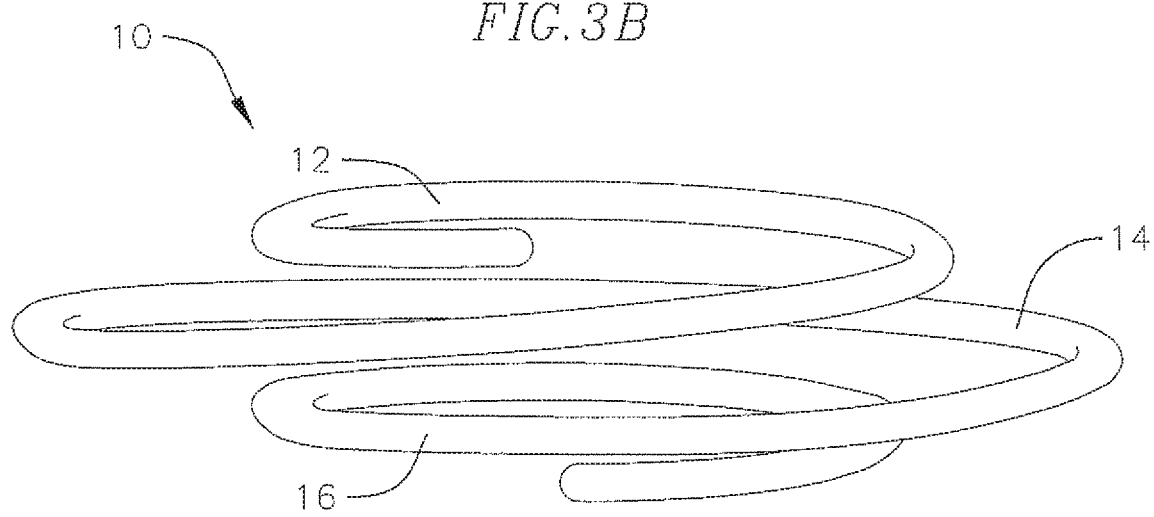

FIGS. 3A and 3B illustrate an embodiment of a helical or coil anchoring device according to an embodiment of the invention. The illustrated embodiment shows a helical anchor 10 that has three turns. However, in other embodiments, other helical anchors can have more or less turns depending on the particular application and the anatomy of the patient. The helical anchor 10 includes an upper first turn 12, a central second turn 14, and a lower third turn 16, and defines a space extending through the center of the helical anchor 10. The upper and lower turns 12, 16 of the anchor 10 are smaller than the central turn 14. In one embodiment, the smaller end turns 12, 16 of the helix are approximately 25 mm in diameter and the larger central turn 14 is approximately 35 mm in diameter when the anchor 10 is unbiased. However, in other embodiments, the sizes of the turns 12, 14, and 16 can be different, so long as the central turn 14 is larger than the end turns 12, 16. In embodiments with more than three turns, more than one central turn can be sized to be greater than the end turns, or there can be more than one smaller sized turn at either end of the anchor, or both. Furthermore, in some embodiments, the upper and lower turns of the anchor can have different diameters from one another.

In one embodiment, the helical anchor 10 is made from a shape memory material, such as nitinol, which will facilitate straightening of the anchor 10 for easier delivery inside a patient. In other embodiments, the anchor 10 can be made from or include one of various other biocompatible metals or of other biocompatible materials.

In addition, the core material of the helical anchor 10 can be covered by a biocompatible fabric or other biocompatible materials, to improve the stability, biocompatibility, or other functionality of the anchor 10 after it has been implanted inside the patient. Such fabrics or other covers can also serve to promote contact or friction between a stent and/or prosthetic valve with the anchor 10, to reduce the expansion of the anchor 10, and to tighten the grip of the anchor 10 on a stent or prosthetic valve that is inflated or expanded inside of it, as discussed in greater detail below.

FIG. 4A to 4C schematically show steps of inserting a balloon expandable stent into the coiled anchor 10 discussed above. FIG. 4A first shows a cross-sectional view of the anchor 10 prior to expansion of the stent or a prosthetic valve inside the anchor. Similarly as discussed above with respect to FIGS. 3A and 3B, the anchor 10 includes three turns, where the central turn 14 has a greater diameter than the end turns 12 and 16.

In FIG. 4B, a balloon 30 is inserted through the central space 18 defined by the anchor 10 and is then inflated inside the helical anchor 10 to a size that is greater than the diameter of at least one of the end turns 12, 16 of the anchor 10. In addition, the balloon 30 carries with it an expandable stent 20 that is positioned through the center of the anchor 10 before the balloon 30, and the stent 20 positioned thereon, are expanded, and the stent 20 impacts or otherwise comes into contact with the helical anchor 10.

Since the balloon is expanded to a size that is greater than the diameter of the end turns 12, 16 of the anchor 10, the expansion of the balloon 30 and the stent 20 inside the anchor 10 results in an increase in the diameters of the two end turns 12, 16. For example, where the end turns 12, 16 have an unbiased diameter of 25 mm, the balloon 30 and stent 20 can expand to up to 27 mm wide, and urge the end turns 12, 16 radially outwardly, so that the end turns are also expanded to approximately 27 mm wide. Meanwhile, as the two end turns 12, 16 are expanded, they pull on the ends of the larger central turn 14 of the anchor 10, and cause the larger central turn 14 to instead reduce in diameter. Therefore, after inflation of the balloon 30 and stent 20 inside the anchor 10, in one embodiment, the turns of the anchor 10 all end with approximately the same diameter, which in the example above is about 27 mm.

After the stent 20 has been expanded through the center of the anchor 10, the balloon 30 can be deflated and removed. FIG. 4C schematically shows a final configuration of the anchor 10 with the stent 20 expanded therethrough, after the balloon 30 has been removed. The stent 20 is held in position in the anchor 10 by the radial pressure or friction formed between the stent 20 and the turns of the anchor 10.

The stent 20 in FIG. 4C is shown with a fabric cover. The cover can cover the inside or the outside of the stent 20, or both. In other embodiments, the stent does not include a cover or other covering layer. Polyester or one of various other materials can be used for the stent cover. In other embodiments, biologic coverings, such as pericardium derived from an animal or human materials, can also be used.

Meanwhile, the stent 20 itself can be made from a stainless steel or an alloy of stainless steel, as is typically used in medical implants, or from one of various other biocompatible metals or other materials. A wide variety of stent designs can be compatible and used on conjunction with the helical anchor 10 in the method described above.

Friction between the stent 20 with at least the smaller turns of the helical anchor 10, and/or with undersides of mitral valve leaflets that are pinched between the anchor 10 and the stent 20, holds the stent 20 in position within the anchor 10. Furthermore, the larger central turn 14 can be drawn closer to the stent 20 to a degree where the central turn 14 also abuts and applies pressure against an outer surface of the stent 20. Along these same lines, when the smaller end turns 12, 16 of the anchor 10 are held more securely against the stent 20 during expansion, and movement or slippage is reduced between these surfaces, the larger central turn 14 of the anchor 10 can be pulled radially inwardly more rapidly or effectively. Therefore, surface coatings and/or other treatments or options that improve the contact or friction between the smaller turns of the anchor 10 and the stent 20 will increase the rate of reduction in diameter of the largest turn or turns of the anchor 10, leading to a tighter or more secure fixation between the parts. In one embodiment, one or more of the smaller turns of the anchor 10 has hooks, barbs, or other attachment mechanism to improve engagement with the stent 20.

Figure 5A:
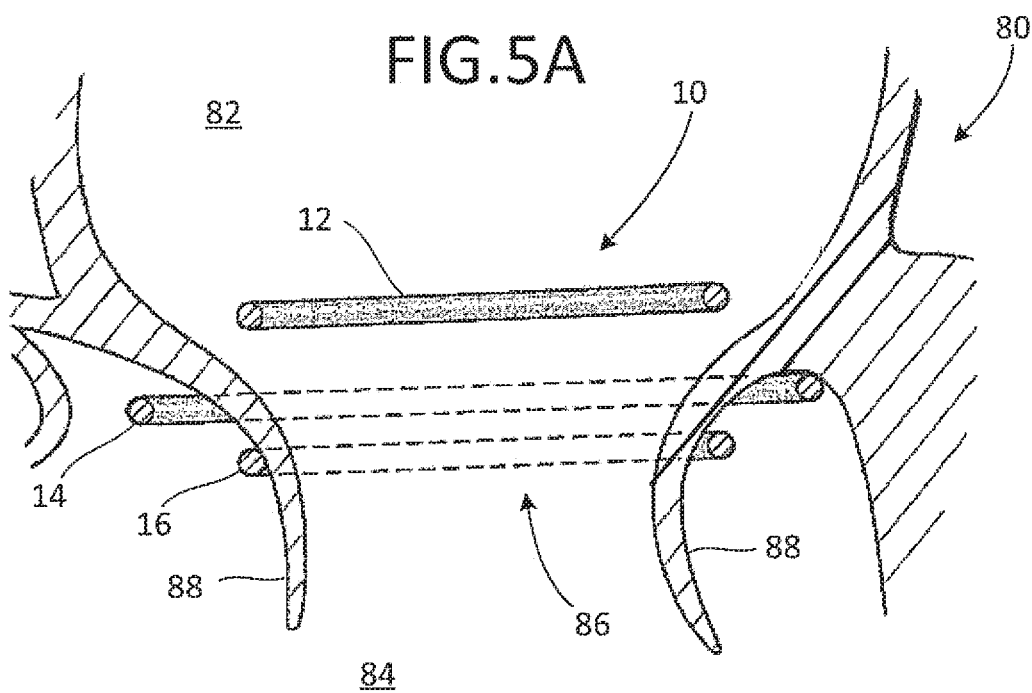
FIGS. 5A-5C show steps of implanting a coil anchor and a balloon expandable stent at a native mitral valve according to an embodiment of the invention.
Figure 5B:
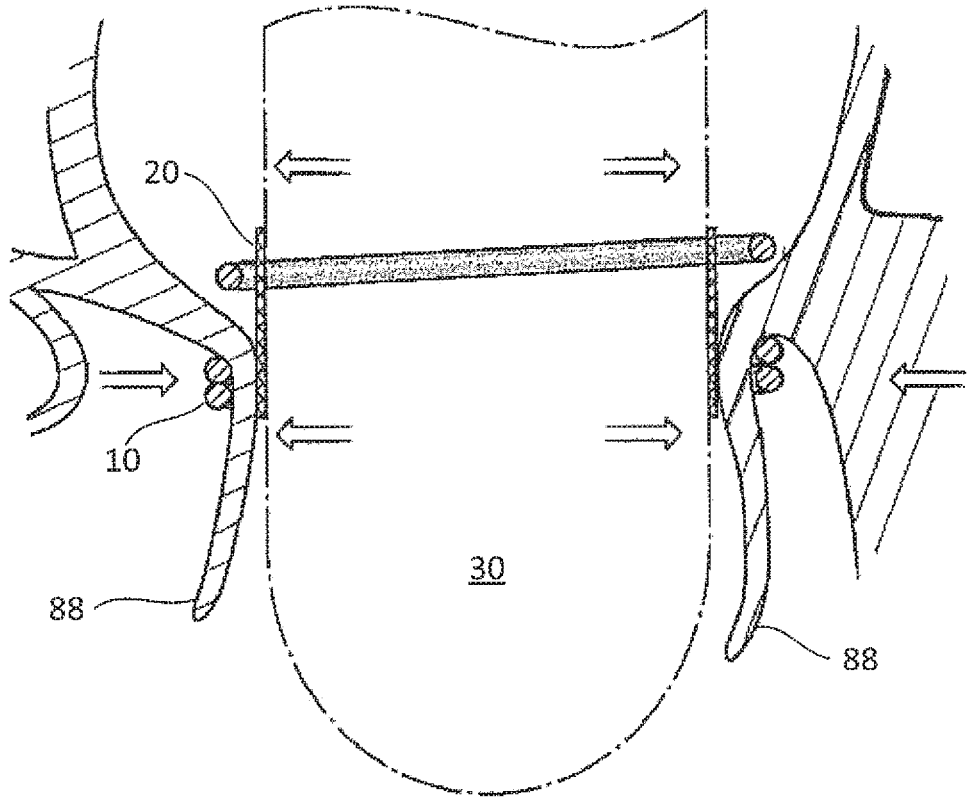
Figure 5C:
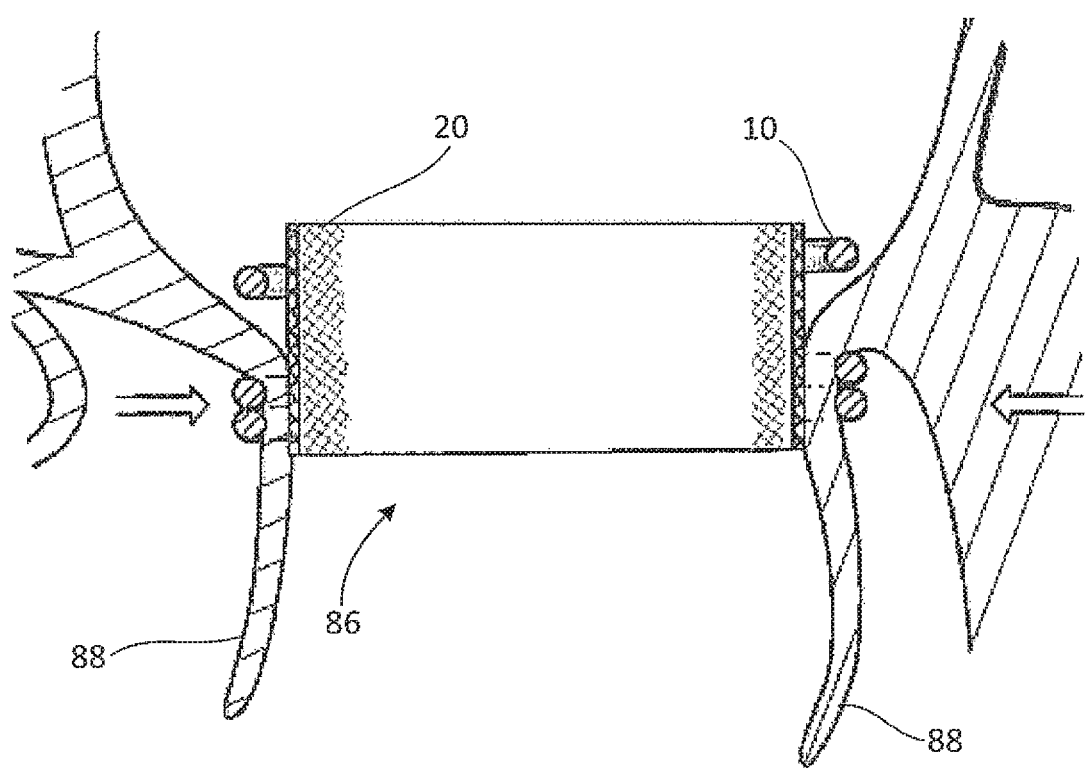

FIGS. 5A to 5C show steps of implanting the coil anchor 10 and stent 20 inside a patient's heart 80, at the native mitral valve annulus 86. The native mitral valve annulus of a patient suffering from mitral regurgitation or other mitral valve leakage can be dilated, in some cases to about 35 mm. The dilated size of different diseased mitral valves can vary, and different anchors and/or stents can be utilized according to the dilated sizes or the desired sizes of the patient's native mitral valve, to treat each particular diseased valve accordingly.

In FIG. 5A, the coil anchor 10 has already been delivered inside the heart, for example, via an apical or transseptal procedure, an endovascular or transcatheter procedure, or one of various other known procedures. When the anchor 10 is in position around the native mitral valve annulus 86, two turns of the anchor 10, the lowest small turn 16 and the central larger turn 14, are located beneath the mitral valve 86, and inside the left ventricle 84. Meanwhile, the upper smaller turn 12 is located inside the left atrium 82. In other embodiments, a different combination of turns can be positioned in the left atrium 82 and the left ventricle 84, based on the application as desired by the practitioner.

In general, the larger turn 14 of the helical anchor 10 can be selected to match the diameter of the patient's enlarged mitral annulus 86, so that the anchor 10 can rest around the mitral valve annulus 86 without exerting undue pressure on the native mitral valve leaflets 88 or other portions of the mitral valve annulus 86, prior to introduction of a stent or prosthetic valve therethrough. The smaller turns 12, 16 of the anchor 10 can be selected based on the amount of shortening that is desired of the larger turn 14. In other words, the larger turn 14 can be selected based on the size of the enlarged mitral valve 86 in the diseased patient, and the size of the smaller turns 12, 16 can be selected to dictate the desired size the larger turn 14 of the anchor 10 will be reduced to, and thereby determine approximately the desired size of the treated mitral valve annulus 86 after implantation. Furthermore, the sizes and shapes of the turns 12, 14, 16 of the coiled anchor 10 can also be selected to facilitate easier placement and positioning of the anchor 10 around the native mitral valve leaflets 88 and/or the chordae tendineae (not shown) when the anchor 10 is first deployed.

After the anchor 10 is positioned at a desired location around the native mitral valve annulus 86, a balloon 30 is used to expand the anchor 10, as seen in FIG. 5B. Similarly as seen in FIG. 4B, the balloon 30 carries and delivers an expandable stent 20, which can be covered with a cover layer, as previously discussed. The deflated balloon 30 and unexpanded stent 20 are first moved in the space defined by the anchor 10, until the stent 20 is positioned at the desired location through the anchor 10.

The balloon 30 is then inflated to expand the stent 20, and this expansion causes a radially outward pressure to be applied against at least the smaller coils 12, 16 of the anchor 10. Similarly as discussed above, inflation of the balloon 30 and expansion of the stent 20 in the anchor 10 result in expansion of the lowest and highest turns 12, 16 of the anchor 10, and reduction in diameter of the larger central turn 14 of the anchor 10. The motion of the turns, and the amount of reduction in size/shape of the larger central turn 14 can be adjusted based on the amount of friction or hold between the smaller turns 12, 16 of the anchor 10 and the stent 20.

As can also be seen in FIG. 5B, since the lower turns 14, 16 are positioned outside of the native mitral valve leaflets 88, and the stent 20 is expanded inside the native mitral valve annulus 86, the valve leaflets 88 are trapped or pinched in position between the lower turns 14, 16 of the anchor 10 and the stent 20.

After the stent 20 has been expanded to its final size in the anchor 10, the balloon 30 can be removed. The stent 20 remains fixed in its expanded position within the anchor 10 after the balloon 30 is removed.

By reducing the size of the larger central turn 14 of the anchor 10 through expansion of the stent 20 therethrough, the size of the native mitral valve annulus 86 has also been reduced. This reduction in size of the valve annulus 86 is schematically shown by the arrows in FIG. 5C. For example, a diameter of a diseased or leaky mitral annulus in a patient can be 35 mm prior to treatment, but after the stent 20 is implanted and expanded in the anchor 10, the central turn 14 of the anchor 10 is reduced to about 27 mm. When the size of the larger central turn 14 of the anchor 10 is reduced, the central turn 14 urges the native valve leaflets 88 inwards, so that the size of the native mitral valve annulus 86 is also reduced from about 35 mm to about 27 mm. By using an anchor 10 and stent 20 or other type of annuloplasty ring in this manner for reducing the size of and/or for reshaping a diseased native mitral valve annulus 86, mitral regurgitation can be eliminated or greatly reduced.

Other mitral annulus variations in other patients or based on other diseases can be paired with anchors 10 and/or stents 20 having different combinations of diameters to produce optimal results for each patient and his or her needs. In each embodiment, there are one or more larger central turns that are surrounded by smaller upper and lower turns, where the larger turn or turns are used to reduce the diameter of the mitral annulus when the system is activated.

Furthermore, in the described embodiment, three complete turns are shown in the anchor 10. However, it is also possible to have an anchor where the upper and lower turns are not full turns. For example, the lower turn 16 shown in the left ventricle 84 can be a half a turn in an alternate embodiment, so that at the end of the procedure, there are less than two turns of the anchor 10 positioned in the left ventricle 84. In some embodiments, the procedure can also be performed with an anchor having only two turns, for example, one large turn and one small turn.

The embodiment in FIGS. 5A to 5C also shows an axial gap between the highest turn 12 and the central turn 14 of the anchor 10. The gap can be useful in providing a longer attachment length for the stent 20, so that there is a larger target in which to position the stent 20 during implantation. The longer length of the anchor 10 can also provide more stability to the system after implantation. In some embodiments, the longer anchor 10 can also facilitate easier initial positioning of the anchor 10 around the native mitral annulus 86. The anchor 10 in other embodiments can have larger or smaller gaps between turns, as desirable. In some embodiments, the anchor can have no gaps between turns. In embodiments with longer anchors, the longer anchors can also facilitate implantation of longer stents. The longer stents, in turn, can provide a larger target for potential valve implantation later.

In some patients, even after an annuloplasty or other mitral valve resizing or reshaping has been performed, there can still be some residual leakage. In some cases, additional measures can still be employed to further reduce leakage or otherwise improve performance of the native mitral valve.

Figure 6A:
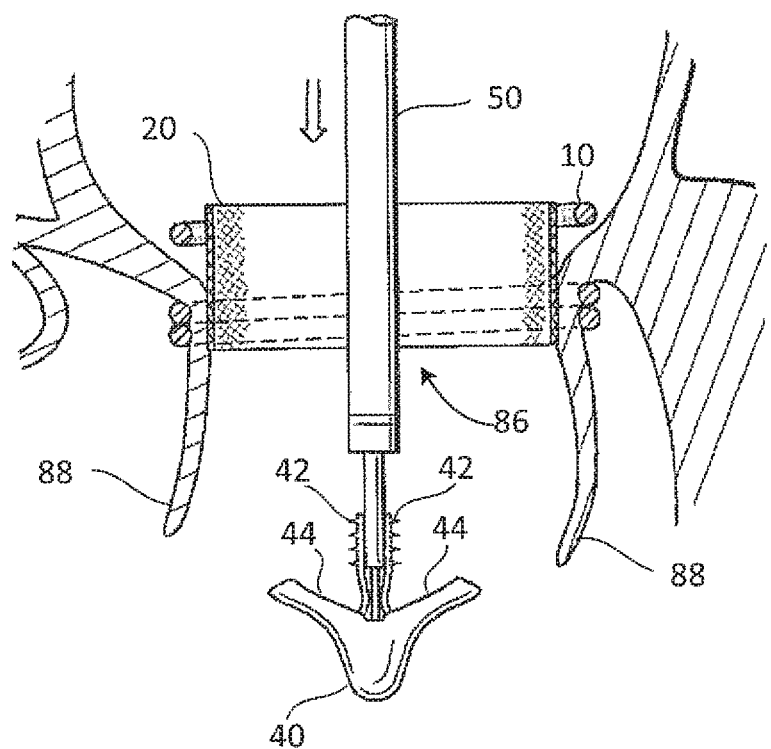
FIGS. 6A and 6B show steps of performing an edge to edge repair on a mitral valve with an implanted stent using a clip according to an embodiment of the invention.
Figure 6B:
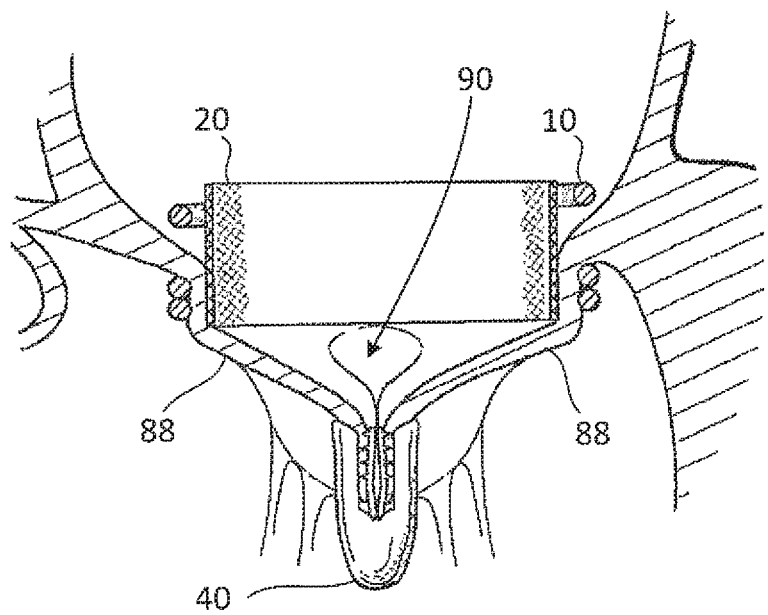

For example, FIGS. 6A and 6B show steps of further treatment on a stented mitral valve where additional leakage reduction is desired. FIG. 6A shows the start of an edge to edge repair on the mitral valve leaflets 88 utilizing a clip 40, to eliminate or reduce any residual leak after an anchor 10 and stent 20 have already been implanted. The clip 40 is being introduced into the left ventricle 84, for example, from the left atrium 82, using one of various known delivery methods and access sites. The clip 40 can be delivered by a tool 50, and is positioned so that ends of the native mitral valve leaflets 88 can be clamped together with clip 40. The clip 40 can include one or more inner clamping surfaces 42 and one or more outer clamping surfaces 44 that are connected via a distal hinge. In the embodiment shown, the clip 40 includes two inner clamping surfaces 42 and two outer clamping surfaces 44. One or both of the clamping surfaces 42, 44 can further include teeth or other surface features to facilitate a more secure clamping of the mitral valve leaflets 88 by the clip 40. In other embodiments, other clipping or clamping devices can also be applied to the native mitral valve leaflets 88 to perform the edge to edge repair procedure.

Figure 7A:
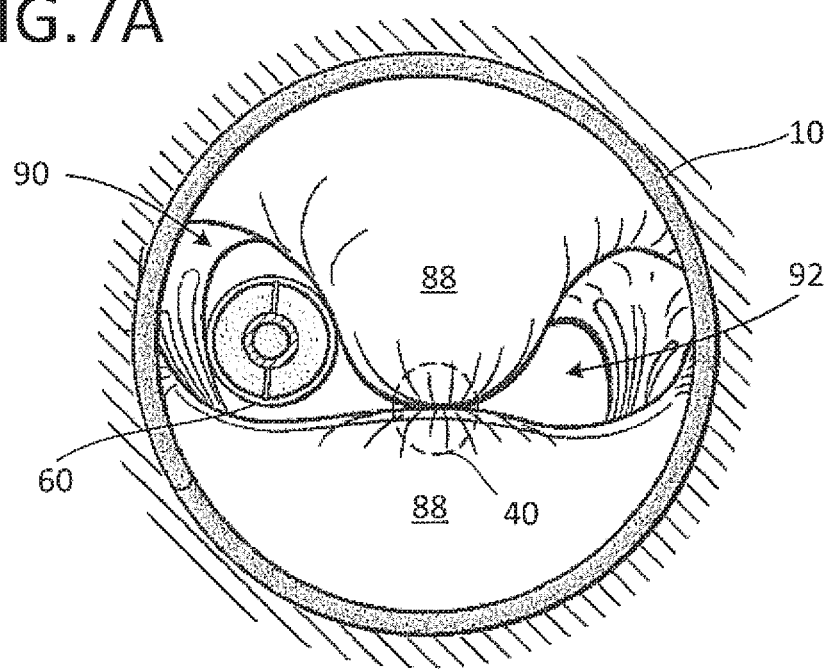
FIGS. 7A and 7B show steps of implanting a prosthetic mitral valve at a native mitral valve annulus where an edge to edge repair was previously performed, according to an embodiment of the invention.

In FIG. 6B, the clip 40 has been closed to attach the free edge of the anterior mitral valve leaflet to the free edge of the posterior mitral valve leaflet. In the example shown, the outer clamping surfaces 44 are pushed towards the inner clamping surfaces 42 to close the clip 40, and each mitral valve leaflet 88 can be pinched or clamped between a corresponding inner clamping surface 42 and a corresponding outer clamping surface 44 of the clip 40. The clip 40 is applied in this embodiment roughly in the middle of the valve orifice (for example, as can be seen in FIG. 7A). In other embodiments, the clip 40 can be applied at any of various different locations on each native mitral valve leaflet 88 based on where leakage is most severe, or where the clip 40 can reduce the most leakage. In some embodiments, more than one clip can be applied, to further reduce leakage through the native valve, as needed.

The end result, as seen in FIG. 6B, is similar to the original Alfieri type procedure, including a combination of an annuloplasty ring made up of an anchor and/or stent for reshaping the native mitral valve annulus, and an edge to edge repair performed on the native mitral valve leaflets. The sequence discussed above is shown with the annuloplasty or native valve reshaping performed first, and the edge to edge repair performed on the native valve leaflets afterwards. However, in other embodiments, the order can be reversed, where a clip is applied first (even if it was performed in conjunction with a previous procedure), and then the annuloplasty or other reshaping or resizing of the valve annulus can be performed thereafter. In procedures where an edge to edge repair is performed first, the inflatable balloon which delivers the stent afterwards can be limited by the presence of the clip, clamp, or other device used for the edge to edge repair. In these situations, a balloon having a shorter length can be used, or the stent can be positioned at a more distal position on the balloon, so that the balloon does not come into contact with the clip, to prevent damage to the clip when the balloon is inflated and the stent is expanded. It is also possible to have a balloon that is bifurcated, or Y-shaped, so that the split ends of the balloon can be positioned around the clip, where one part of the balloon passes through the valve opening on one side of the clip and the other part of the balloon passes through the valve opening on the other side of the clip. For example, referring to FIG. 7A, one end of a bifurcated balloon can pass through orifice 90 of the native valve formed by the clip 40, while the other end of the bifurcated balloon can pass through orifice 92 on the other side of the clip 40.

In some cases, the combination of the annuloplasty or native valve reshaping and the edge to edge repair is still inadequate to curb mitral regurgitation or other mitral valve leakage. The patient may still have an unacceptable leak at the mitral valve even after both of these procedures are undertaken.

Figure 7B:
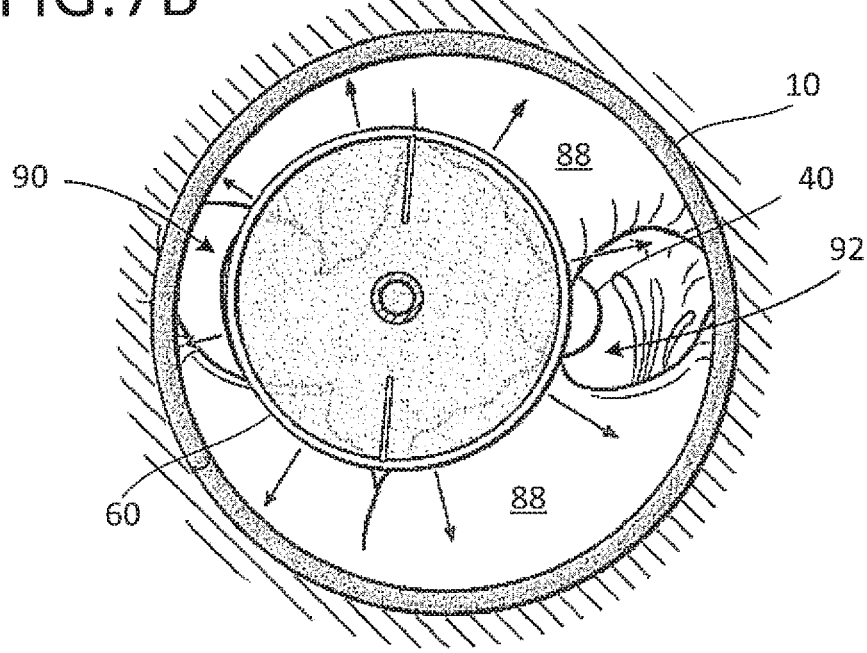
Figure 8:
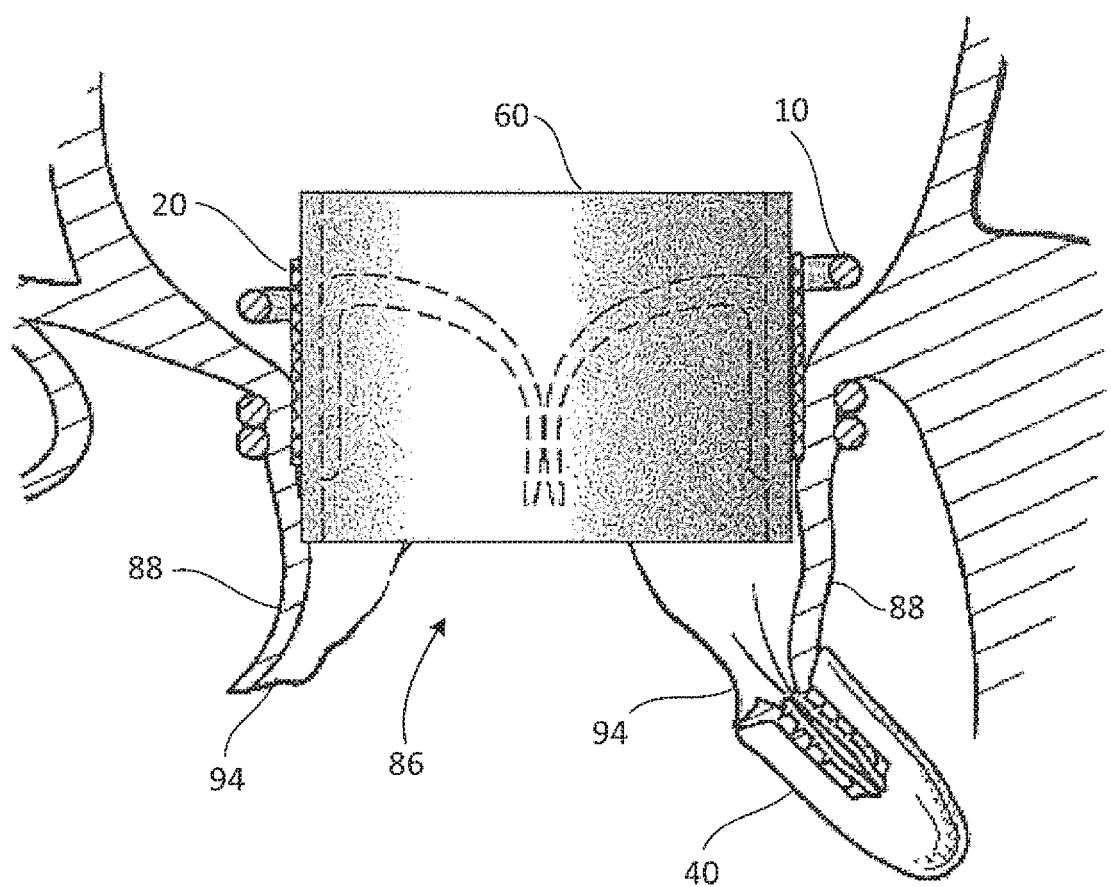
FIG. 8 shows a prosthetic mitral valve fully implanted in a stent at a native mitral valve where an edge to edge repair was previously performed, according to an embodiment of the invention.

FIGS. 7A, 7B, and 8 show how the anchor 10 and/or stent 20 discussed above can also serve as an ideal anchor for a stent mounted prosthetic valve. It is expensive from a regulatory approval and from a stocking standpoint to have many different valve shapes and sizes. The reduction in size of the native mitral annulus by the anchor 10 and/or the stent 20 allows for a smaller sized prosthetic stent valve to be used. Furthermore, the anchor 10 and/or the stent 20 help to reshape the native mitral annulus to be more circular, so that more conventional valves with circular or cylindrical outer profiles that are already on the market can be used at the mitral position. In addition, the heart may be able to function more efficiently or effectively with a smaller annulus diameter at the mitral position, since the mitral valve will not be stretched open as widely and can contract more completely. Therefore, a mitral valve anchor or stent that serves to downsize a native mitral valve annulus to a more uniform shape and/or size can allow for a lower number of valves or variations of valves to be produced, saving costs and simplify the manufacturing and implantation procedures.

FIG. 7A shows a top view of a mitral annulus that has already undergone a reshaping using an anchor 10 and/or a stent (not shown in FIG. 7A), as well as an edge to edge procedure using a clip 40 to clip distal ends of the native mitral valve leaflets 88. The edge to edge repair has formed two orifices 90, 92, at the mitral position on either side of the clip 40, respectively. In some patients, the prior procedures may not prove to be sufficient to curb or reduce the mitral leakage through the mitral valve illustrated in FIG. 7A. Therefore, a balloon that carries a stent mounted prosthetic valve 60 can further be positioned across the mitral valve through one of the mitral orifices 90 or 92. The prosthetic valve 60 that is deployed and implanted can be one of various different known valves with a size and shape suitable for fitting in the anchor 10, for example, the Edwards Lifesciences Sapien XT™ valve.

In FIG. 7B, the prosthetic valve 60 is expanded, for example, via inflation of a balloon delivery system. The expansion of the prosthetic valve 60 places a large radial force or load on the native mitral leaflets 88 that were previously clipped together with the clip 40 during the earlier edge to edge repair. As can be seen in FIG. 7B, the expansion of the prosthetic valve 60 begins displacing the clip 40 and stretching out the native mitral leaflets 88, and eventually, at least one of the leaflets 88 tears away from the clip 40, slips out of the clip 40, or otherwise detaches from the clip 40.

To encourage or promote cutting or tearing of the native mitral valve leaflets 88, the above valve expansion procedure can be preceded by inflation of a separate balloon at the mitral position that cuts the native mitral valve leaflets 88. Similar cutting balloons have been used, for example, to cut away plaques in arteries. Another option can be to cut a defect in at least one of the native mitral valve leaflets 88, and then to advance the stent valve inside or adjacent to the pre-cut portion of the leaflet 88. In other embodiments, the stent in which the prosthetic mitral valve is mounted can have its own cutting features, for cutting surrounding portions of the native mitral leaflets 88, to further facilitate expansion of the prosthetic valve 60.

In some embodiments, the prosthetic valve 60 can be implanted with the clip 40 from the edge to edge repair remaining intact. In such cases, it would be necessary to ensure that an adequately sized orifice is formed in which the prosthetic valve 60 can be positioned, to allow adequate flow into the left ventricle. If there is an obstruction to flow, or if the orifice is not sufficiently sized, the clip 40 can still be cut from one edge of the mitral valve leaflets 88 thereafter, to form a more suitable orifice or opening for the prosthetic valve 60.

In some cases, it is possible that the clip 40 detaches from both of the native mitral leaflet edges 88. This would be highly unusual since it would mean that the retention of the clip 40 on both leaflets was virtually identical. However, in such instances, the clip 40 can be easily retrieved and removed from the patient.

Generally, after one of the native mitral leaflets 88 is ripped or torn from the clip 40, the prosthetic valve is free to expand until it abuts against the anchor 10 and/or the stent 20. FIG. 8 shows the prosthetic valve 60 after it has been fully expanded. The valve 60 sits securely inside the prior annuloplasty apparatus including the anchor 10 and the stent 20. The pre-positioned anchor 10 and stent 20 provide an excellent target for insertion and expansion of the prosthetic valve 60. The annuloplasty apparatus can be clearly visible on fluoroscopy.

As previously discussed, one of the native mitral leaflets 88 has been torn or ripped or otherwise detached from the clip 40 at the tear 94, and the functionality of the native mitral leaflets 88 has been replaced by the prosthetic valve 60. The clip 40, which has detached from one of the native mitral leaflets 88, is shown inside the left ventricle 84, and should not affect the functionality of the prosthetic valve 60.

In other embodiments, various different features from the different embodiments discussed above can also be combined or modified, based on the needs of each individual patient. For example, the annuloplasty or mitral annulus reshaping procedure does not need to be performed in conjunction with an edge to edge procedure. Instead, the annuloplasty or mitral reshaping can be a standalone procedure. In addition, if the annuloplasty procedure is not adequate to remedy a diseased heart, and the leakage seems too severe to be solved by implantation of one or more clips via an edge to edge repair, it is also possible to proceed directly from annuloplasty or mitral reshaping to implantation of a prosthetic mitral valve inside the anchor and/or the stent used for the annuloplasty or mitral reshaping.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially can in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms can vary depending on the particular implementation and are readily discernible by one of ordinary skill in the art.

In view of the many possible embodiments to which the principles of the disclosure can be applied, it should be recognized that the illustrated embodiments are only preferred examples and should not be taken as limiting the scope of the disclosure. Rather, the scope of the disclosure is defined by the following claims.

What is claimed is:

1. A method for delivering an implant to reshape a native mitral valve of a heart, the implant comprising a coiled anchor having a first end, a second end, and a central axis extending between the first and second ends, wherein the coiled anchor defines an inner space coaxial with the central axis and comprises a first turn defining a central portion of the inner space having a first width, a second turn connected to the first turn at the first end of the coiled anchor and defining a portion of the inner space having a width that is smaller than the first width, and a third turn connected to the first turn at the second end of the coiled anchor and defining another portion of the inner space having a width that is smaller than the first width, and a stent comprising an expandable frame, the method comprising:
   positioning the coiled anchor at a native mitral valve of a heart of a patient, such that at least a portion of the first turn of the coiled anchor is positioned in a left ventricle of the heart and around valve leaflets of the native mitral valve;
   positioning the stent at the native mitral valve through the inner space of the coiled anchor when the stent is in a collapsed state; and
   expanding the stent, wherein the stent is expandable to a width that is greater than the width of the inner space defined by at least one of the second turn or the third turn when the coiled anchor is unbiased, such that a radially outward pressure is applied by the stent on the at least one of the second turn or the third turn to increase the width of the portion of the inner space defined by the at least one of the second turn or the third turn, while the width of the portion of the inner space defined by the first turn is decreased to a width that is smaller than the first width.

2. The method of claim 1, wherein after expansion of the stent in the coiled anchor, the widths of the respective portions of the inner space defined by the first turn, the second turn, and the third turn, are substantially equal to one another.

3. The method of claim 1, further comprising applying a clip to ends of the valve leaflets of the native mitral valve for drawing the ends of the valve leaflets closer to one another.

4. The method of claim 3, further comprising:
   positioning a prosthetic valve comprising an expandable frame and housing a plurality of leaflets through the expanded stent when the prosthetic valve is in a collapsed state; and
   expanding the prosthetic valve, wherein the prosthetic valve is expandable to a width that is at least the width of the expanded stent, such that a radially outward pressure is applied by the frame of the prosthetic valve on the stent to hold the prosthetic valve in the stent.

5. The method of claim 4, further comprising detaching the end of at least one of the valve leaflets of the native mitral valve from the clip.

6. The method of claim 1, further comprising:
   positioning a prosthetic valve comprising an expandable frame and housing a plurality of leaflets through the expanded stent when the prosthetic valve is in a collapsed state; and
   expanding the prosthetic valve, wherein the prosthetic valve is expandable to a width that is at least the width of the expanded stent, such that a radially outward pressure is applied by the frame of the prosthetic valve on the stent to hold the prosthetic valve in the stent.

7. The method of claim 1, wherein the stent houses a plurality of valve leaflets for controlling blood flow therethrough.

8. A method for delivering an implant to reshape a native valve of a heart, the implant comprising a coiled anchor having a first end, a second end, and a central axis extending between the first and second ends, wherein when unbiased, the coiled anchor defines an inner space coaxial with the central axis and comprises a first turn defining a central portion of the inner space having a first width, a second turn connected to the first turn at the first end of the coiled anchor and defining a portion of the inner space having a second width that is smaller than the first width, and a third turn connected to the first turn at the second end of the coiled anchor and defining another portion of the inner space having a third width that is smaller than the first width, and a stent comprising an expandable frame, the method comprising:
   positioning the coiled anchor at a native valve of a heart of a patient, such that at least a portion of the first turn of the coiled anchor is positioned in a ventricle of the heart and around valve leaflets of the native valve;
   positioning the stent at the native valve through the inner space of the coiled anchor when the stent is in a collapsed state; and
   expanding the stent, wherein the stent is expandable to a fourth width that is greater than at least one of the second width and the third width, such that a radially outward pressure is applied by the stent on the second turn and the third turn such that the portion of the inner space defined by the second turn is wider than the second width and the portion of the inner space defined by the third turn is wider than the third width, while the portion of the inner space defined by the first turn is decreased to a width that is smaller than the first width.

9. The method of claim 8, wherein after expansion of the stent in the coiled anchor, widths of the respective portions of the inner space defined by the first turn, the second turn, and the third turn, are substantially equal to one another.

10. The method of claim 8, further comprising applying a clip to ends of the valve leaflets of the native mitral valve for drawing the ends of the valve leaflets closer to one another.

11. The method of claim 10, further comprising:
positioning a prosthetic valve comprising an expandable frame and housing a plurality of leaflets through the expanded stent when the prosthetic valve is in a collapsed state; and
expanding the prosthetic valve, wherein the prosthetic valve is expandable to a width that is at least the width of the expanded stent, such that a radially outward pressure is applied by the frame of the prosthetic valve on the stent to hold the prosthetic valve in the stent.

12. The method of claim 11, further comprising detaching the end of at least one of the valve leaflets of the native mitral valve from the clip.

13. The method of claim 8, further comprising:
positioning a prosthetic valve comprising an expandable frame and housing a plurality of leaflets through the expanded stent when the prosthetic valve is in a collapsed state; and
expanding the prosthetic valve, wherein the prosthetic valve is expandable to a width that is at least the width of the expanded stent, such that a radially outward pressure is applied by the frame of the prosthetic valve on the stent to hold the prosthetic valve in the stent.

14. The method of claim 8, wherein the stent houses a plurality of valve leaflets for controlling blood flow therethrough.

* * * * *